United States Patent [19]
Oksman et al.

[11] Patent Number: 5,260,727
[45] Date of Patent: Nov. 9, 1993

[54] WIDE DEPTH OF FOCUS INTRAOCULAR AND CONTACT LENSES

[76] Inventors: Henry C. Oksman, 20 Wagon Wheel Rd., Mamaroneck, N.Y. 10543; Joseph Eisner, 185 East 85th St., New York, N.Y. 10028

[21] Appl. No.: 601,853

[22] Filed: Oct. 22, 1990

[51] Int. Cl.$^5$ .............................................. G02C 7/04
[52] U.S. Cl. .................................... 351/162; 351/161
[58] Field of Search ............... 351/160 R, 160 H, 161, 351/162, 177; 623/6

[56] References Cited

U.S. PATENT DOCUMENTS

| | | | |
|---|---|---|---|
| 3,339,997 | 9/1967 | Wesley | 351/161 |
| 3,794,414 | 2/1974 | Wesley | 351/161 |
| 4,576,453 | 3/1986 | Borowsky | 351/162 |
| 4,637,697 | 1/1987 | Freeman | 351/161 |
| 4,666,640 | 5/1987 | Neefe | 351/162 X |
| 4,778,462 | 10/1988 | Grendahl | 351/161 X |
| 4,795,462 | 1/1989 | Grendahl | 351/161 X |
| 4,798,608 | 1/1989 | Grendahl | 351/161 X |
| 4,798,609 | 1/1989 | Grendahl | 351/161 X |
| 4,840,477 | 6/1989 | Neefe | 351/162 |
| 4,955,904 | 9/1990 | Atebara et al. | 623/6 |

OTHER PUBLICATIONS

Shannon & Wtatt, Applied Optics and Optical Engineering, vol. VIII (1980).
Mino & Okano, Improvement in the OTF of a Defocused Optical System through the use of Shaded Apertures, Applied Optics, Oct. 1971, vol. 10, No. 10, pp. 2219–2225.

*Primary Examiner*—Scott J. Sugarman
*Attorney, Agent, or Firm*—Fiddler Levine & Mandelbaum

[57] ABSTRACT

A lens and method of fabrication thereof for increasing depth of focus where the lens power can be a constant but the amplitude and phase of the wave across the pupillary aperture are variables. The lens can be constructed by shading regions thereof in accordance with a mathematical function, e.g., a Gaussian distribution or Bessel function over a predetermined geometry, such as e.g., concentric, parallel or radial. The lens may be of single power or multiple power, e.g., of the bi-focal type.

19 Claims, 4 Drawing Sheets

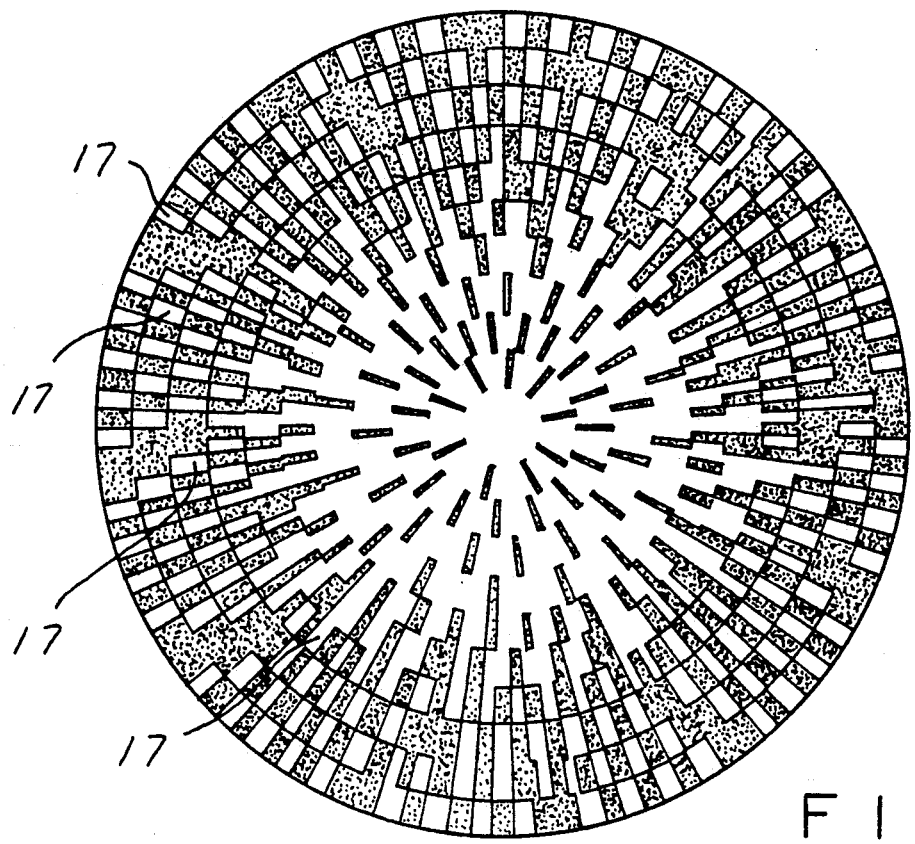
F I G. 3
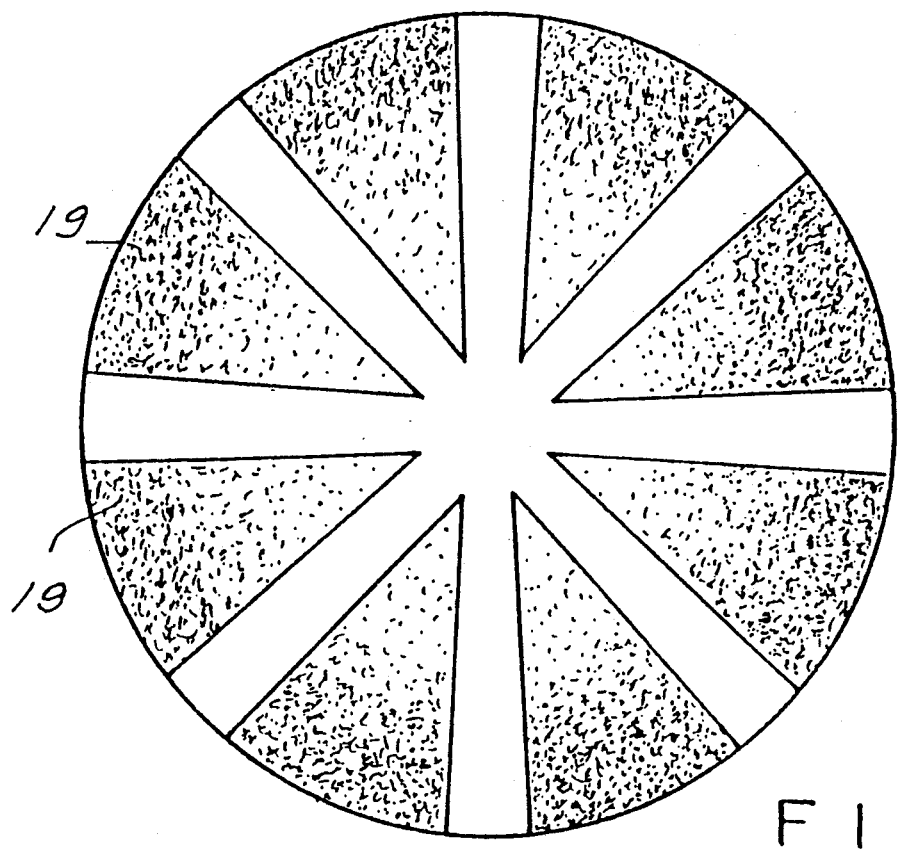
F I G. 5

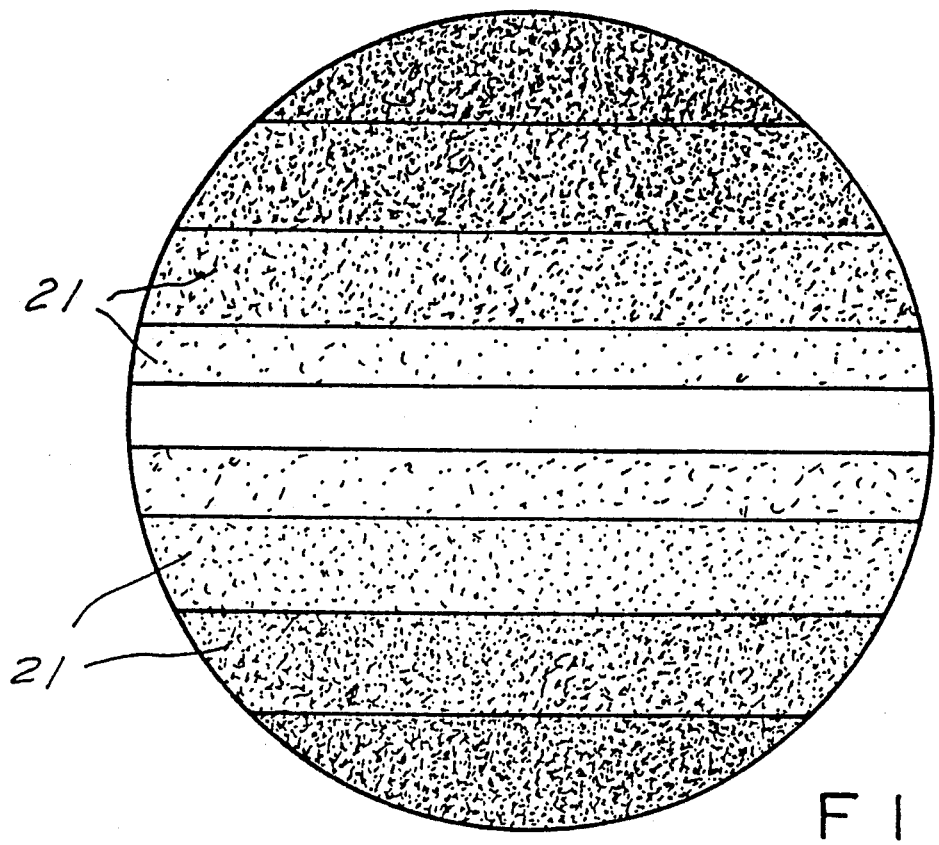
F I G. 6
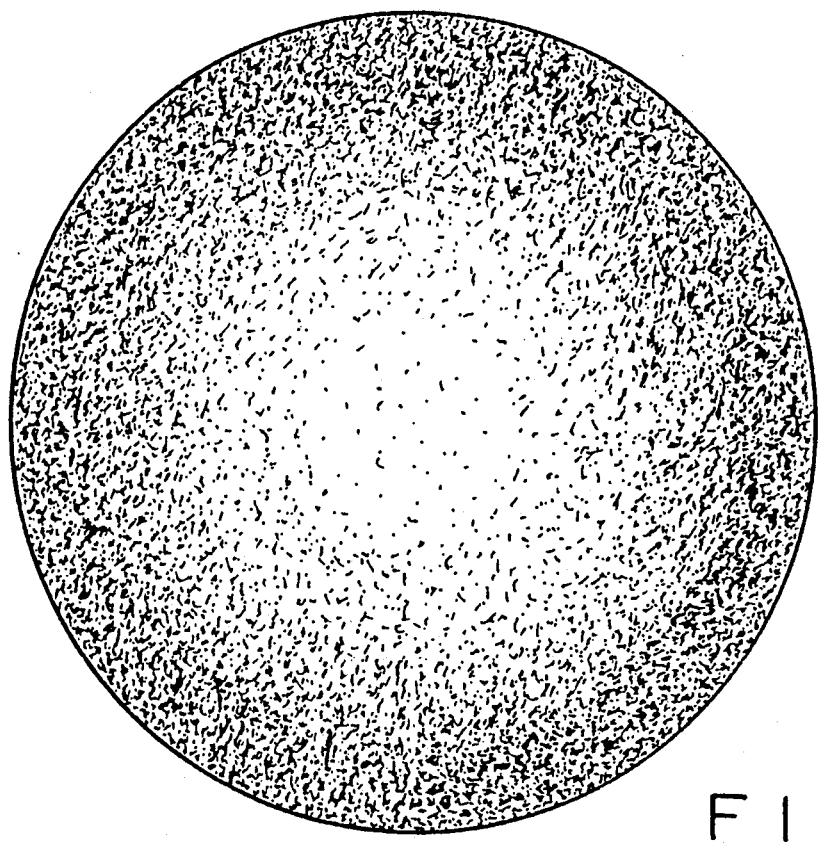
F I G. 7

WIDE DEPTH OF FOCUS INTRAOCULAR AND CONTACT LENSES

BACKGROUND OF THE INVENTION

It is known in the art of eye care to correct abnormal vision by use of lenses and to alter focus of an image on the retina of the eye. Such lenses can be worn in frames as conventional eye glasses, worn on the surface of the eye as contact lenses, or implanted within the eye as intraocular lenses where a large degree of abnormal vision must be corrected.

Prior art corrective lenses are of fixed power, having a single measure of diopter correction over the entire viewing area of the lens in the case of monofocal lenses, or two or more zones of different fixed diopters in the case of bifocal, multifocal and progressive lenses. Prior art bifocal and multifocal lenses are designed following add power principles. In the case of common eye glasses, two or more differing diopter or power zones many be disposed at vertically displaced regions when the lens is worn to enable the wearer to direct his or her line of sight through the appropriate region depending on the optical distance of the subject to be viewed.

In the case of non-displaced contact lenses and implants, it is not possible t o vary the line of sight with respect to the disposition of the corrective lens. Such lenses have zones with different powers disposed either concentrically or with other geometries at the pupillary plane. This type of construction is illustrated in U.S. Pat. No. 4,637,697 to Freeman for Multifocal Contact Lenses Utilizing Defraction and Refraction. The limited depth of focus of such lenses results in viewing through plural power lenses simultaneously so that the image is, at best, only partially in focus, irrespective of its distance from the viewer.

Other prior art lenses employ phase shift variation between two powers so as to cause destructive and constructive interference at only one very specific given location. In locations other than this on-axis point, there is deviation from the above interference pattern which results in imperfect focusing. These lenses are clear, i.e., have greater than 90% transmission, but a large percent of their power is not focused. Energy which is not focused not only fails to contribute to the focusing of the image, but it actually degrades the image. Such multi-power lenses blur vision and the resulting distractive effect makes their utility questionable. The latter approach is illustrated in U.S. Pat. No. 4,636,211 to Nielsen for a Bifocal Intra-Ocular Lens.

It is also known in the art to color a portion of a contact lens simulating the iris of the eye about a transparent central opening for light to enter the pupil of the eye. This is done for cosmetic purposes and has no appreciable effect on vision. U.S. Pat. No. 4,840,477 to Neefe for Dyed Color Change Contact Lens illustrates this type of construction.

Another use of colored lenses is disclosed in U.S. Pat. No. 3,339,997 to Wesley for Bifocal Ophthalmic Lens having Different Color Distance and Near Vision Zones. There, Wesley teaches the construction of a bifocal ophthalmic lens wherein zones tinted to have different colors are used to focus in the near and distant regions respectively. Wesley depends on the fact that light rays adjacent one end of the visible spectrum focus at a different point than light rays adjacent the other end.

It is also known in the art that depth of focus can be expanded by narrowing the effective pupillary aperture. In the ideal pinhole case, the depth of field is infinite. If two pinholes are used to view an object, an increase in two point discrimination is observed and depth of focus decreases. However, illumination, which is a function of the square of the radius of the pinhole aperture, is severely limited. This solution is also an impractical one in most cases because of diffraction.

An attempt by Wesley to overcome the restricted field of view of pinhole lenses is described in the text entitled Contact Lenses by Philips and Stone, published by Batterworth, in 1989. The text illustrates Wesley's use of opaque portions on lenses to enhance vision according to arbitrary patterns and without reference to any specific mathematical function. Lenses with pluralities of light transmitting apertures surrounded by opaque areas are employed in various symmetric patterns which appear to have been arbitrarily conceived. These patterns which utilize neither gradual shading nor light transmission according to a predetermined mathematical function are believed to be substantially ineffective for failure to control light transmission in accordance with suitable mathematical functions, e.g., a Bessel or Gaussian function.

SUMMARY OF THE INVENTION

The instant invention overcomes the aforementioned problems of prior art lenses, particularly as applied to patients who can not accommodate their vision in order to see objects over a large depth of field such as pseudophakic and presbyopic patients. More specifically the invention includes a lens adapted to be worn on the eye or implanted in the eye for enabling viewing with an extended depth of focus, including a substrate having a surface with a plurality of regions of at least partial transparency, at least one of the regions having a degree of transparency different than that of another of the regions, wherein the first and second regions can be disposed in a predetermined geometry, e.g., concentric, parallel, radial, and the transparency of the regions varies as a mathematical function of their distance from a predetermined origin, e.g., by a Bessel function or Gaussian distribution, the substrate having a tint applied to at least one of the regions to attenuate its transparency. The substrate can be contoured so that at least one of the regions has a non-zero diopter power.

It is therefore an object of the invention to provide a lens adapted to be worn in front of the pupil, such as a contact lens or anterior chamber implant, or in back of the iris, such as a posterior chamber lens implant, for enabling viewing over an extended depth of field.

Another object of the invention is to provide a lens on the eye or implanted in the eye adapted to be worn for enabling viewing over an extended depth of field which permits but does not require contouring of the lens for diopter power.

Still another object of the invention is to provide a lens adapted to be worn on the eye or implanted in the eye for enabling viewing over an extended depth of field by shading selected regions of the lens substrate.

A further object of the invention is to provide a lens adapted to be worn on the eye or implanted in the eye for enabling viewing over an extended depth of field by shading selected regions of the lens substrate to vary transparency as a mathematical function of the location of the regions and to cause phase shifts.

DESCRIPTION OF THE DRAWINGS

FIG. 3 is a plan view of the apparatus of a second preferred embodiment of the invention.

FIG. 5 is a plan view of the apparatus of a fifth preferred embodiment of the invention.

FIG. 6 is a plan view of the apparatus of a sixth preferred embodiment of the invention.

FIG. 7 is a plan view of the apparatus of a seventh preferred embodiment of the invention.

DESCRIPTION OF THE PREFERRED EMBODIMENTS

This invention is based on electromagnetic wave theory. Depth of focus afforded by a lens may be measured by applying a Fourier transform to the integral of the transmitted light intensity times the light transmitting aperture surface area. Variations of shade opacity which are not in accordance with a specific mathematical function will have poor multifocality. The result of a Fourier transform analysis of the transmission of such lenses discloses no significant increase in depth of field.

Lenses made according to the invention need only have a single power with transmission variations and phase variations across the pupillary plane. Lenses can have zero power or single standard powers, e.g., $-3.00$ or $+20.00$, and depth of focus can be managed with respect to these powers. The lenses can be contact lenses, or intraocular lenses, with transmission variations that are continuous (analog) or discrete (digital). Lens shapes can be biconvex, planoconvex, meniscus, or of other configurations. The invention can be applied to virtually any lens design and lens manufacturing technology and to variable power, bifocal, and multifocal lenses.

The image transmitted to the retina is a function of the integral of the light at the focal plain and is independent of pupil geometry in monofocal lenses. Expansion of depth of field is achieved by shading the lens at the optical zone (pupillary area) as set forth below. Lens shading for widening the depth of field can be applied to a lens with regular optics (monofocal) or to virtually any lens with special optics. Shading can be done with a permanent die or a die that selectively varies transmission, e.g., as a function of intensity of illumination.

Figure 1:
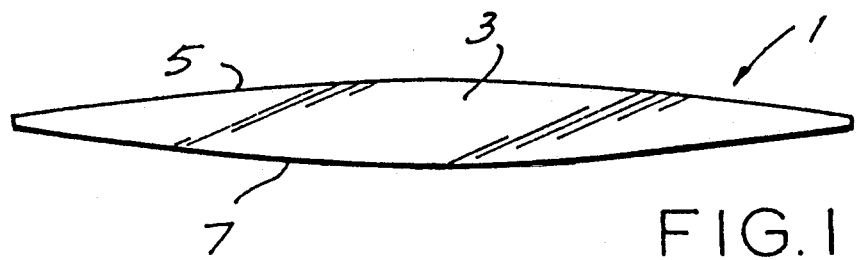
FIG. 1 is an elevation view of the apparatus of a first preferred embodiment of the invention.

Referring now to FIG. 1 of the drawings there is shown a lens 1 formed from a substrate 3 having an upper surface 5 and a lower surface 7. The thickness of the lens 1 is substantially constant over its entire area and its power, measured in diopters, is zero.

Figure 2:
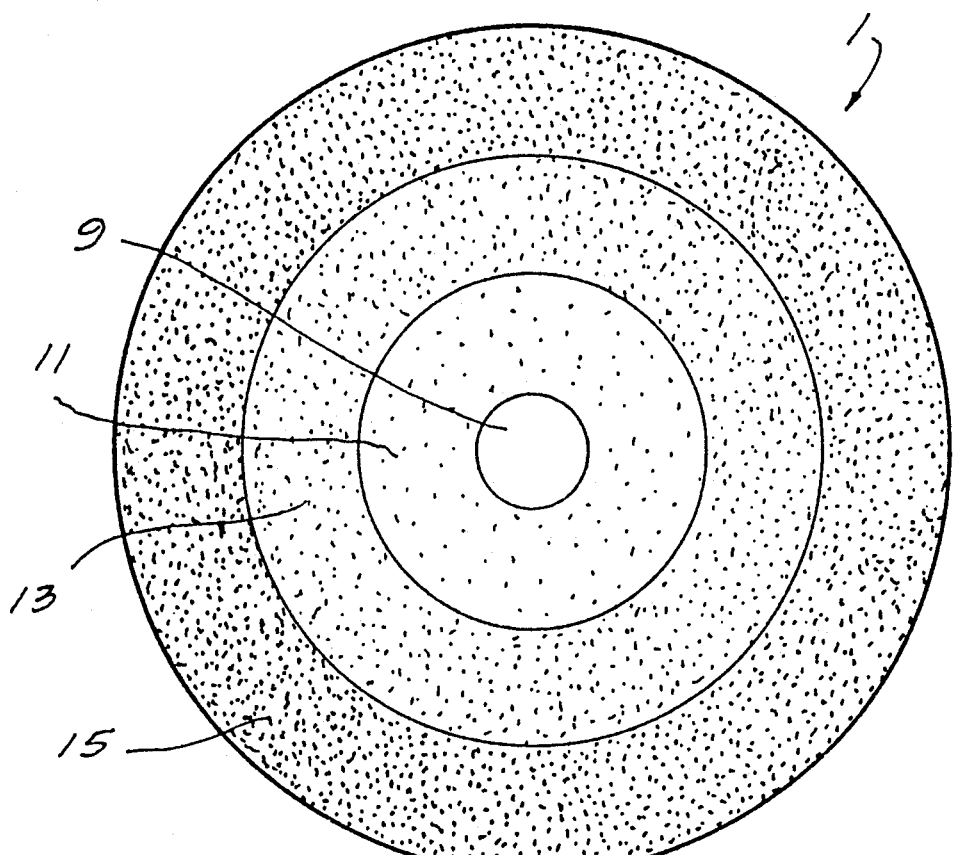
FIG. 2 is a plan view of the apparatus of the first preferred embodiment of the invention.

Referring additionally to FIG. 2, it is seen that the lens 1 is tinted to provide differing constant degrees of transparency through concentric circular bands or regions. For example concentric region 9, at the center of the lens 1 has a greater transparency than adjacent concentric region 11 which in turn has a greater transparency than adjacent concentric region 13, and so on to the outermost concentric region 15.

The differing transparencies may be imparted to the lens by conventional tinting techniques whereby dyes are applied in varying densities, or by etching of the lens surface. Dynamic variations in the absolute and relative transparencies of the lens 1 may be achieved by using photosensitive dyes which decrease in transparency in response to increases in intensity of incident light.

For ease of fabrication, it is possible to achieve variable density from one region to another by tinting with dyes of a single density and transparency in alternating zones 17 as can be seen in FIG. 3. By keeping the ratio of the area of each tinted zone to the areas of the adjacent untinted zones within each region constant, and varying the ratios from one concentric region to another, the relative overall transparencies of the regions in the lens of FIG. 3, which have a predetermined mathematical relationship, can be made to approximate the relative overall transparencies of the regions in the lens of FIG. 2.

The tint can be partially transparent or may even be entire opaque to light. The larger the number of light sampling zones into which each region is divided in the "digital" lens of FIG. 3, the closer is the approximation to the mathematical distribution governing the transparency of the continuously tinted "analog" lens of FIG. 2. Hence, proceeding radially inwardly from the outermost region of the lens of FIG. 3 to the innermost region, the ratio of transparent zone area to tinted or opaque zone area increases. The result is an overall increase in light transmission from one region to the next in the radial inward direction just as in the case of the continuously tinted regions of the lens of FIG. 2.

The degree by which the overall transparencies of the shaded regions differ from one to the other determines the depth of focus of the lens. Shading the regions so that the amplitudes of their light transmissions follow a Gaussian distribution function theoretically results in a lens having Gaussian depth of field characteristics.

In the case where the shading of the lens follows a Gaussian distribution, i.e., in the form of $Ae^{-aR^2}$, where A = a constant, as close to 1 as can be achieved and preferably greater than 0.96, a = a distribution constant that is inversely proportional to depth of field, and R = the distance from the center of the lens, the result is an elongated focal plane with a truly wide depth of focus.

Figure 4A:
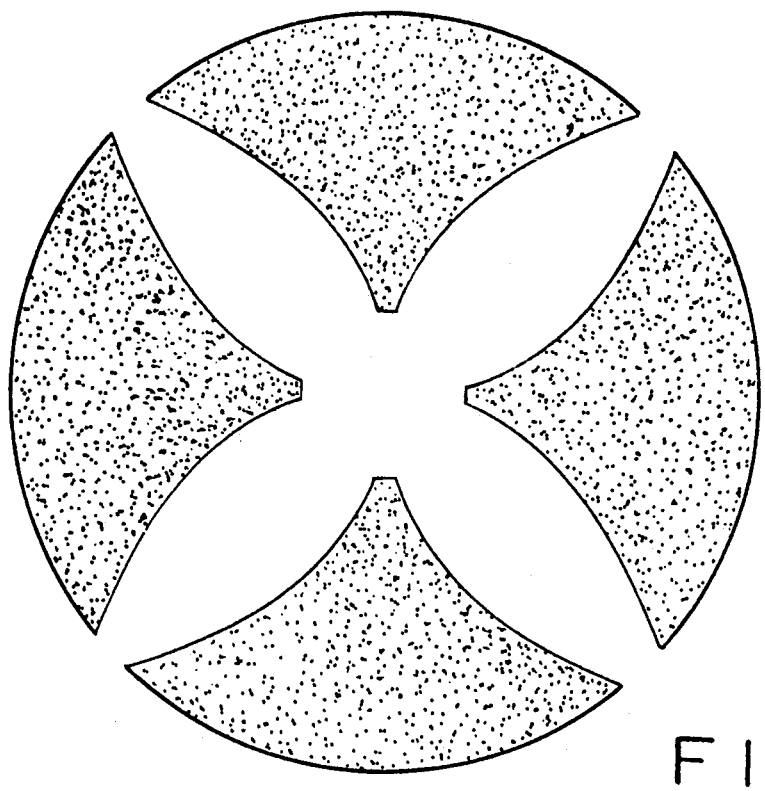
FIG. 4a is a plan view of the apparatus of a third preferred embodiment of the invention.
Figure 4B:
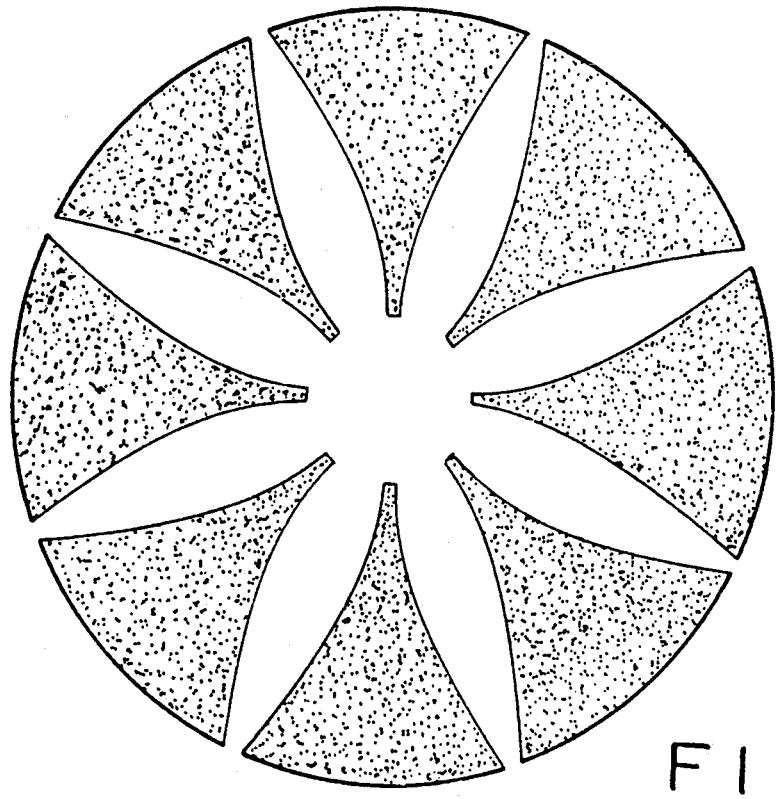
FIG. 4b is a plan view of the apparatus of a fourth preferred embodiment of the invention.

Another example of simulation of variable shading according to a continuous mathematical function through the use of discrete regions of transparency and opacity is shown in FIGS. 4a and 4b. In the lens of FIG. 4a, a circular lens three (3) millimeters in diameter is arbitrarily divided into four quadrants of ninety degrees (90°) each. In each quadrant, the percentage of transparent area is determined as a function of distance from the center of the lens according to the Gaussian relationship described above as:

Light Transmission = $Ae^{-aR^2}$, where $A=1$, $a=0.715$, and $0.6 < R < 1.5$ mm.

The central circular area of the lens up to a radius of 0.6 mm is of maximum transparency in the illustration of FIG. 4a. The Gaussian function can apply to a lens construction through its entire area, e.g., for $0 < R < 1.5$ in the case of a lens having a 3 mm diameter.

The parameters of the 4-sector lens of FIG. 4a are used in the lens of FIG. 4b except that the lens of FIG. 4b is arbitrarily divided into eight (8) sectors. As the number of discrete sectors increases, with each sector area decreasing, the continuous shading configuration of the type illustrated in FIG. 7, described below, is approached.

Shading the regions so that the amplitudes of their light transmissions follow a Bessel function theoretically results in an infinite depth of field. However, in practical designs using a Bessel function algorithm, the resulting lens will have a finite depth of field due to the finite size of the lens or pupil.

Other geometries than the ones of FIGS. 2 and 3 may be employed to effect concentric regions of differing transparency. For example, as shown in FIG. 5, tinted inwardly directed angularly displaced wedges 19 provide a digital approximation of the concentric regions of transparency of the lens of FIG. 2, similar in effect to the lens of FIG. 3 yet permitting the tinting to be applied in larger continuous zones than the scattered zones of the lens of FIG. 3. This geometry can be advantageous in obtaining the high degree of control over regional transparency that the digital technique of FIG. 3 permits while realizing economies in fabrication.

The geometry of the lens shading need not necessarily be a circular one. Rectangular systems may be used as in the case of the lens illustrated in FIG. 6. There, the adjacent shaded regions are parallel. The lens of FIG. 6 may be shaded to enhance depth of focus over the field of view by increasing transparency of the shaded regions 21 along a direction transverse to them from opposite edges of the lens toward the center. This arrangement can be used to enhance depth of focus in the vertical field of view without affecting relative changes in depth of focus across the lateral field of view.

Lenses following the teachings of the invention need not be subdivided into discrete zones. Continuous shading over the entire lens may be employed. For example, in the lens of FIG. 7, the density of the shading is continuous, that is, it increases radially over entire lens surface which constitutes a single zone.

With lenses constructed in accordance with the heretofore described invention, the energy in the caustic zone is very low in comparison with known prior art designs. With conventional lenses that rely on power variation, there is no capability for achieving zero power in the caustic region. The lenses of the invention permit the caustic region to approach zero power and the lenses can achieve true wide depth of focus without blur.

It is to be appreciated that the foregoing is a description of seven preferred embodiments of the invention to which variations and modifications may be made without departing from the spirit and scope of the invention. For example, other geometric patterns and relative densities of shading may be applied in accordance with other mathematical functions having Fourier transforms consistent with enhanced depth of focus.

What is claimed is:

1. A lens adapted to be worn on, or implanted in, the eye comprising a substrate having a surface with a plurality of regions of at least partial transparency, at least one of said regions having a degree of transparency greater than another of said regions more distant from the center of said lens than said one region for enabling viewing with an extended depth of focus.

2. A lens according to claim 1 wherein said first and second regions are concentrically displaced.

3. A lens according to claim 1 wherein said first and second regions are in parallel disposition.

4. A lens according to claim 1 wherein said first and second regions are radially displaced.

5. A lens according to claim 1 wherein said first and second regions are angularly displaced.

6. A lens according to claim 1 wherein the transparency of said regions varies as a mathematical function of their distance from a predetermined origin.

7. A lens according to claim 6 where said mathematical function is a Gaussian distribution.

8. A lens according to claim 6 where said mathematical function is a Bessel function.

9. A lens according to claim 1 wherein said substrate comprises a tint applied to at least one of said regions to attenuate its transparency.

10. A lens according to claim 9 wherein the transparency of said tint is variable as a function of the light incident upon it.

11. A lens according to claim 1 wherein said substrate is contoured so that at least one of said regions has diopter power the absolute value of which is greater than zero.

12. A method of increasing depth of focus for a lens adapted to be worn on, or implanted in, the eye comprising rendering the transparency of at least one of a plurality of regions of at least partial transparency of said lens greater than the transparency of another of said regions more distant from the center of said lens than said one region.

13. A method of increasing depth of focus for a lens according to claim 12 wherein the transparencies of concentrically displaced regions are rendered different.

14. A method of increasing depth of focus for a lens according to claim 12 wherein the transparencies of parallel displaced regions are rendered different.

15. A method of increasing depth of focus for a lens according to claim 12 wherein the transparencies of radially displaced regions are rendered different.

16. A method of increasing depth of focus for a lens according to claim 12 wherein the relative transparencies of said regions are rendered to vary as a mathematical function of their distance from a predetermined origin.

17. A method of increasing depth of focus for a lens according to claim 16 wherein said mathematical function is a Gaussian distribution.

18. A method of increasing depth of focus for a lens according to claim 16 wherein said mathematical function is a Bessel function.

19. A method of increasing depth of focus for a lens according to claim 12 further comprising tinting said one region to a different transparency than said another region.

* * * * *